US011103542B2

(12) United States Patent
Ranganathan

(10) Patent No.: US 11,103,542 B2
(45) Date of Patent: *Aug. 31, 2021

(54) COMPOSITION AND METHOD FOR MAINTAINING HEALTHY KIDNEY FUNCTION

(71) Applicant: Kibow Biotech, Inc., Newtown Square, PA (US)

(72) Inventor: Natarajan Ranganathan, Broomall, PA (US)

(73) Assignee: KIBOW BIOTECH, INC., Newtown Square, PA (US)

( * ) Notice: Subject to any disclaimer, the term of this patent is extended or adjusted under 35 U.S.C. 154(b) by 676 days.

This patent is subject to a terminal disclaimer.

(21) Appl. No.: 15/393,664

(22) Filed: Dec. 29, 2016

(65) Prior Publication Data

US 2017/0106029 A1  Apr. 20, 2017

Related U.S. Application Data

(63) Continuation-in-part of application No. 13/937,527, filed on Jul. 9, 2013, now Pat. No. 9,655,932, which is a continuation-in-part of application No. 13/602,386, filed on Sep. 4, 2012, now Pat. No. 8,481,025, which is a continuation of application No. 12/407,201, filed on Mar. 19, 2009, now Pat. No. 8,257,693, which is a continuation of application No. 10/936,262, filed on Sep. 8, 2004, now abandoned, which is a continuation-in-part of application No. PCT/US02/07554, filed on Mar. 13, 2002.

(51) Int. Cl.

| | |
|---|---|
| *A61K 35/744* | (2015.01) |
| *A61K 35/747* | (2015.01) |
| *A61K 35/745* | (2015.01) |
| *A61K 31/733* | (2006.01) |
| *A61K 45/06* | (2006.01) |
| *A61K 9/48* | (2006.01) |
| *A61K 9/00* | (2006.01) |
| *A23L 33/15* | (2016.01) |
| *A23P 10/30* | (2016.01) |
| *A23L 33/10* | (2016.01) |
| *A23L 33/105* | (2016.01) |
| *A61K 31/702* | (2006.01) |
| *A61K 35/742* | (2015.01) |
| *A61K 31/198* | (2006.01) |

(52) U.S. Cl.
CPC .......... *A61K 35/744* (2013.01); *A23L 33/10* (2016.08); *A23L 33/105* (2016.08); *A23L 33/15* (2016.08); *A23P 10/30* (2016.08); *A61K 9/0053* (2013.01); *A61K 9/48* (2013.01); *A61K 31/198* (2013.01); *A61K 31/702* (2013.01); *A61K 31/733* (2013.01); *A61K 35/742* (2013.01); *A61K 35/745* (2013.01); *A61K 35/747* (2013.01); *A61K 45/06* (2013.01); *A23V 2002/00* (2013.01); *A23Y 2220/03* (2013.01); *A23Y 2240/75* (2013.01); *A23Y 2300/55* (2013.01)

(58) Field of Classification Search
None
See application file for complete search history.

(56) References Cited

U.S. PATENT DOCUMENTS

| | | | |
|---|---|---|---|
| 4,022,883 A | 5/1977 | Setala | 424/93 |
| 4,218,541 A | 8/1980 | Ackerman | 435/262 |
| 4,569,846 A | 2/1986 | Ohzeki et al. | 426/40 |
| 4,871,539 A | 10/1989 | Hata et al. | 424/93.3 |
| 4,970,153 A | 11/1990 | Kobashi et al. | 435/128 |
| 5,116,737 A | 5/1992 | McCoy | 435/42 |
| 5,258,181 A | 11/1993 | Cregier et al. | 424/738 |
| 5,358,729 A | 10/1994 | Ohkuma et al. | 426/567 |
| 5,716,615 A | 2/1998 | Vesely et al. | 424/93.4 |
| 5,756,088 A | 5/1998 | Matsuura et al. | 424/93.4 |
| 5,902,743 A | 5/1999 | Luchansky et al. | 435/252.1 |
| 5,952,021 A | 9/1999 | Santus | 426/34 |
| 5,976,580 A | 11/1999 | Ivey et al. | 426/2 |
| 6,162,831 A | 12/2000 | Kelly et al. | 514/646 |
| 6,203,797 B1 * | 3/2001 | Perry | A61K 31/198 424/639 |
| 6,306,442 B1 | 10/2001 | Sunvold et al. | 424/725 |
| 7,993,903 B2 | 8/2011 | Hayakawa et al. | 435/252.1 |
| 7,998,470 B2 | 8/2011 | Ranganathan | 424/93.1 |
| 8,257,693 B2 | 9/2012 | Ranganathan | 424/93.3 |
| 8,481,025 B2 | 7/2013 | Ranganathan | 424/93.3 |
| 2002/0090416 A1 | 7/2002 | Connolly | 426/2 |
| 2007/0207187 A1 | 9/2007 | Yajima et al. | 424/439 |
| 2009/0252709 A1 | 10/2009 | Nose et al. | 424/93.4 |
| 2011/0171283 A1 | 7/2011 | Riesinger | 424/445 |

FOREIGN PATENT DOCUMENTS

| | | | |
|---|---|---|---|
| EP | 1145643 A1 | 10/2001 | |
| JP | H08310960 A | 11/1996 | |
| WO | WO 99/49877 | 10/1999 | |
| WO | WO 00/71138 A2 | 11/2000 | |
| WO | WO 00/71139 A2 | 11/2000 | |
| WO | WO-0070964 A1 * | 11/2000 | ........... A61K 31/721 |
| WO | WO 00/72855 A2 | 12/2000 | |
| WO | WO 00/74689 A1 | 12/2000 | |
| WO | WO 00/74712 A2 | 12/2000 | |
| WO | WO 05/032591 | 4/2005 | |
| WO | WO 07/140622 A1 | 12/2007 | |

OTHER PUBLICATIONS

Gibson et al. "Dietary Modulation of the Human Colonic Microbiota: Introducing the Concept of Prebiotics" Journal of Nutrition 1995 125:1401-1412.

Office Communication dated Dec. 23, 2005 from U.S. Appl. No. 10/936,262, filed Sep. 8, 2004.

(Continued)

*Primary Examiner* — Susan Hoffman
(74) *Attorney, Agent, or Firm* — Licata & Tyrrell P.C.

(57) ABSTRACT

A delayed-release composition composed of a *Lactobacillus* bacterium, *Bifidobacterium longum*, *Streptococcus thermophlus*, inulin and xylooligosaccharide is provided for use in reducing nitrogenous waste products in the blood and treating renal failure.

6 Claims, No Drawings

(56) References Cited

OTHER PUBLICATIONS

Office Communication dated Feb. 8, 2006 from U.S. Appl. No. 10/936,262, filed Sep. 8, 2004.
Office Communication dated Jul. 25, 2006 from U.S. Appl. No. 10/936,262, filed Sep. 8, 2004.
Office Communication dated Nov. 9, 2006 from U.S. Appl. No. 10/936,262, filed Sep. 8, 2004.
Office Communication dated Mar. 16, 2007 from U.S. Appl. No. 10/936,262, filed Sep. 8, 2004.
Office Communication dated Aug. 29, 2007 from U.S. Appl. No. 10/936,262, filed Sep. 8, 2004.
Office Communication dated Nov. 23, 2007 from U.S. Appl. No. 10/936,262, filed Sep. 8, 2004.
Office Communication dated Mar. 13, 2008 from U.S. Appl. No. 10/936,262, filed Sep. 8, 2004.
Office Communication dated Aug. 21, 2008 from U.S. Appl. No. 10/936,262, filed Sep. 8, 2004.
Office Communication dated Dec. 15, 2008 from U.S. Appl. No. 10/936,262, filed Sep. 8, 2004.
Office Communication dated Sep. 22, 2009 from U.S. Appl. No. 10/936,262, filed Sep. 8, 2004.
Office Communication dated May 27, 2010 from U.S. Appl. No. 12/407,201, filed Mar. 19, 2009.
Office Communication dated Oct. 12, 2010 from U.S. Appl. No. 12/407,201, filed Mar. 19, 2009.
Office Communication dated Feb. 17, 2011 from U.S. Appl. No. 12/407,201 filed Mar. 19, 2009.
Office Communication dated Mar. 22, 2011 from U.S. Appl. No. 12/407,201, filed Mar. 19, 2009.
Office Communication dated Aug. 15, 2011 from U.S. Appl. No. 12/407,201, filed Mar. 19, 2009.
Office Communication dated Nov. 16, 2011 from U.S. Appl. No. 12/407,201, filed Mar. 19, 2009.
Office Communication dated Jan. 27, 2012 from U.S. Appl. No. 12/407,201, filed Mar. 19, 2009.
Office Communication dated Jan. 9, 2013 from U.S. Appl. No. 13/602,386, filed Sep. 4, 2012.
International Preliminary Report on Patentability from PCT/US02/07554, dated Mar. 12, 2002, PCT.
International Search Report from PCT/US02/07554, dated Sep. 13, 2002, PCT.
Natarajan et al. "Probiotic Amelioration of Azotemia in $5/6^{th}$ Nephrectomized Sprague Dawley Rats" The Scientific World Journal 2005 5:652-660, XP055209289.
Extended EP Search Report in Application No. 11832930.9, dated Sep. 2, 2015, EP.
http://www.everydayhealth.com/gout-prevention-possible.apsx—accessed Feb. 2016.
Office Communication dated Jan. 6, 2016 from U.S. Appl. No. 13/937,527, filed Jul. 9, 2013.
Office Communication dated Feb. 29, 2016 from U.S. Appl. No. 13/937,527, filed Jul. 9, 2013.

* cited by examiner

COMPOSITION AND METHOD FOR MAINTAINING HEALTHY KIDNEY FUNCTION

INTRODUCTION

This application is a continuation-in-part application of U.S. Ser. No. 13/937,527, filed Jul. 9, 2013, now U.S. Pat. No. 9,655,932, which is a continuation-in-part application of U.S. Ser. No. 13/602,386, filed Sep. 4, 2012, now U.S. Pat. No. 8,481,025, which is a continuation of U.S. Ser. No. 12/407,201 filed Mar. 19, 2009, now U.S. Pat. No. 8,257,693, which is a continuation of U.S. Ser. No. 10/936,262 filed Sep. 8, 2004, now abandoned, which is a continuation-in-part of U.S. Serial No. PCT/US2002/007554 filed Mar. 13, 2002.

BACKGROUND OF THE INVENTION

One of the main functions of the normal, healthy kidney, besides its regulatory, endocrine, and metabolic functions, is the disposal of waste products. Any impairment of excretory function can lead to the accumulation of a variety of nitrogenous waste products including, urea, creatinine and uric acid. High concentrations of waste products in the blood stream can exacerbate renal failure and promote kidney stones. Moreover, nitrogenous solutes in the circulating blood promote osmotic diffusion into the lumen because of the concentration gradient across the intestinal wall. This diffusion mechanism led to the concept of oral sorbents to augment gut-based clearance of nitrogenous waste products. Sorbents or microbes have demonstrated their ability to remove various compounds and nitrogenous wastes within the large bowel.

Urea-specific sorbents such as synthetic polymers and modified polysaccharides have been evaluated for the removal of urea and other nitrogenous wastes via the gut. Other sorbents such as oxidized starch, activated charcoal, and carob flour have also been investigated for the in vivo elimination of uremic toxins with some success. Prakash & Chang ((1996) *Nature Medicine* 2:883-88) demonstrated that microencapsulated, genetically-engineered *E. coli* DH5 are effective in removing urea and ammonia in an in vitro system. The same researchers obtained similar results in oral administration of *E. coli* DH5 cells in a uremic rat animal model. Bliss et al. ((1996) *Am. J. Clin. Nutr.* 63:392-398) have demonstrated that supplemental gum arabic fiber increases fecal nitrogen excretion and lowers urea nitrogen concentration in chronic renal failure patients consuming a low protein diet. Reinhart et al. ((1998) *Rec. Adv. In Canine and Feline Nutr. Iams Nutrition Symposium Proceedings.* Vol. II:395-404) found that canine renal patients fed a diet containing a fermentable fiber blend improved clinical end-stage renal disease status, suggesting that specific nutritional alteration allows repartitioning of nitrogen excretion away from the kidney and into the feces by colonic fermentation or additional bacterial growth.

U.S. Pat. No. 5,756,088 teaches a prescription diet for the prevention and treatment of dog and cat dermatosis comprising a composition containing a poly-unsaturated fatty acid such as γ-linolenic acid, γ-linolenic acid and docosahexaenoic acid, and/or biotin, and an antiflatulent such as a lactic acid bacterium, a *Bifidobacterium*, a *Lactobacillus*, a butyric acid bacterium or a *Bacillus*, and optionally an oligosaccharide.

U.S. Pat. No. 7,993,903 teaches a composition for inhibiting cholesterol absorption in the intestinal tract, wherein the composition includes *Bifidobacterium*, and optionally a *Lactobacillus* bacterium and carbohydrate.

US 2011/0171283 teaches a composition containing at least one nutrient, at least one disinfecting or decontaminating and/or at least one proteases inhibiting substance and/or complex of substances incorporated in an absorbent dressing for external care and/or treatment of wounds to a human or animal. In one embodiment, the protease inhibiting substance includes non-pathogenic acid producing micro-organisms (e.g., *bifidobacteria*, lactococci, or lactobacilli) and/or synbiotics (e.g., xylooligosaccharide).

US 2009/0252709 teaches a preventive or therapeutic agent for gastritis or ulcer, which includes as an active ingredient *Bifidobacterium bifidum*. This reference teaches that other microorganisms (e.g., *Bifidobacterium* or *Lactobacillus* bacteria), as well as sugars such as xylooligosaccharide.

WO 2007/140622 teaches a probiotic composition containing a mixture of a *Propionibacterium*, a *Lactobacillus*, a *Bifidobacterium* and a *Streptococcus*, wherein said composition can further include a prebiotic.

SUMMARY OF THE INVENTION

The present invention provides a delayed-release composition comprising or consisting of *Lactobacillus acidophilus*, *Streptococcus thermophilus*, *Bifidobacterium longum*, xylooligosaccharide and inulin. In some embodiments, the *Streptococcus thermophilus* is selected for the ability to affect at least a 50% reduction in urea concentrations within 24 hours. In other embodiments, the composition is a capsule. In a further embodiment, the *Lactobacillus acidophilus*, *Streptococcus thermophilus*, *Bifidobacterium longum* are present at a ratio of 1:1:1. In still further embodiments, the composition further includes a vitamin and/or a reducing agent such as glutathione or glutamine. Methods of removing nitrogenous waste product and treating renal failure using the delayed-release composition are also provided.

DETAILED DESCRIPTION OF THE INVENTION

Nitrogenous waste products accumulating in the blood stream have detrimental affects on health. Removal of nitrogenous wastes by diverting them into the colon is a viable approach to decrease the negative impact that waste product accumulation has on an individual's physiology. The present invention combines the properties of probiotic and prebiotic components into a synbiotic product or composition to effectively reduce the blood concentration of nitrogenous waste products and has the added beneficial effect of promoting the growth of desirable intestinal microflora.

A probiotic component of the present invention refers to a mono or mixed culture of live or freeze-dried microorganisms which, when provided to man or animal, beneficially affects the host by improving the properties of the indigenous microflora, such as *bifidobacterium* organisms that metabolize undigested carbohydrates and are beneficial to an individual. Probiotic components of the present invention are selected for their ability to exert a beneficial effect on the host, survive transit through the intestinal tract, to adhere to intestinal epithelial cell lining, to produce antimicrobial substances against pathogens and/or to stabilize the intestinal microflora. Furthermore, a probiotic component should have a good shelf-life. Synbiotic products of the present invention generally contain a large number of viable cells at the time of consumption, and are non-pathogenic and nontoxic. In accordance with this invention, the probiotic component of the invention includes a *Lactobacillus* spp. (e.g., *bulgaricus, acidophilus, lactis, helveticus, casei, plantarum, reuteri, delbrueckii, chamnosus, johnsonii, paracasei*), a *Streptococcus* spp. (e.g., *thermophilus, diacetilactis, cremoris, durans, faecalis*) and a *Bifidobacterium* spp. (e.g., *bifidum, longum, infantis*). In particular, a composition of the invention includes *Lactobacillus acidophilus, Streptococcus thermophilus, Bifidobacterium longum*.

Microorganisms also useful in the invention are those that have the ability, either through natural selection, training or by genetic manipulation, to catabolize various nitrogenous compounds (e.g., urea, creatinine, uric acid and ammonia) by expressing or overexpressing one or more cognate catabolic enzymes. Exemplary microorganisms are those having an elevated level of urease or creatininase secretion as compared to a wild-type microorganism.

A microorganism exhibiting elevated levels of catabolic enzyme secretion can be selected or trained by exposing a selected microorganism on increasing amounts of the metabolite of interest (e.g., urea, creatinine, uric acid and ammonia). For example, it has been found that a standard strain of *Streptococcus thermophilus* can be trained to express elevated levels of urease by sequential passage of the strain on increasing amounts of urea, e.g., a single colony growing on 0.5% urea is selected and applied to medium containing 1.0% urea, a single colony growing on 1.0% urea is selected and applied to medium containing 2.0% urea, etc. Using such a method, a *S. thermophilus* strain having the ability to grow on 5% urea was isolated. This strain proliferated in artificial intestinal fluid (AIF, US Pharmacopeia) in the pH range of 5.5 to 7.5, characteristic of the colon environment; used urea as a sole nitrogen source; and catabolized urea in the presence of other nitrogen sources. It was found that urea hydrolysis was growth- and pH-dependent and that urea concentrations could be reduced by this strain from 300 mg/dL to 20 mg/dL within 24 hours at pH 6.3 when inoculated in AIF at an initial density of $10^9$ cfu/mL. Moreover, this strain survived 3 hours in acidic pH 3.0 with only a one-log loss in cfu and was able to pass through bile. In addition, this strain did not appear to exhibit any resistance to eight commonly used antibiotics. Therefore, these data indicate that a specifically selected or trained bacterial isolate can be used as a urea-targeted component in a synbiotic product of the present invention. Accordingly, certain embodiments of this invention include a bacterium that, by selection or training, is capable of affecting at least an 80%, 70%, 60% or 50% reduction in urea concentrations within 24 hours when cultured in the presence of a urea-containing medium at a pH of about 6 to 7. In certain embodiments, the trained or selected bacterium is *Streptococcus thermophilus*. In other embodiments, the trained or selected bacterium is *Bifidobacterium longum*. In still other embodiments, the trained or selected bacterium is *Lactobacillus acidophilus*.

Elevated levels of urease secretion can also be obtained by overexpressing the gene of interest (e.g., via multiple copies or a promoter driving high levels of expression) in a prokaryotic microorganism of interest such as *Bifidobacterium, Lactobacillus, Streptococcus, Leuconostoc* or *Bacillus*, or a eukaryotic microorganism such as *Saccharomyces*. The gene of interest can be under the regulatory control of an inducible or constitutive promoter. Promoters for use in recombinant prokaryotic expression vectors are well-established in the art and can include the beta-lactamase (penicillinase) and lactose promoter systems (Chang et al. (1978) *Nature* 275:615; Goeddel et al. (1979), *Nature* 281:544), a tryptophan (trp) promoter system (Goeddel et al. (1980) *Nucleic Acids Res.* 8:4057; EPO App. Publ. No. 36,776) and the tac promoter (De Boer et al. (1983) *Proc. Natl. Acad. Sci. USA* 80:21). While these are commonly used promoters which are commercially available, one of skill in the art can appreciate that any other suitable microbial promoter can be used as well. Nucleic acid sequences encoding suitable prokaryotic promoters have been published thereby enabling one of skill in the art to readily isolate these promoters (e.g., by standard cloning or PCR methodologies) for cloning into plasmid or viral vectors (Siebenlist et al. (1980) *Cell* 20:269). The promoter and Shine-Dalgarno sequence (for prokaryotic host expression) are operably-linked to the DNA encoding the gene of interest, i.e., they are positioned so as to promote transcription of the messenger RNA from the DNA, and subsequently introduced into a suitable host cell.

Eukaryotic microbes such as yeast cultures can also be transformed with suitable protein-encoding vectors. See e.g., U.S. Pat. No. 4,745,057. *Saccharomyces cerevisiae* is the most commonly used among lower eukaryotic host microorganisms, although a number of other strains are commonly available. Yeast vectors can contain an origin of replication from the 2 micron yeast plasmid or an autonomously replicating sequence (ARS), a promoter, DNA encoding the desired protein, sequences for polyadenylation and transcription termination, and a gene encoding for a selectable marker. An exemplary plasmid is YRp7, (Stinchcomb et al. (1979) *Nature* 282:39; Kingsman et al. (1979) *Gene* 7:141; Tschemper et al. (1980) *Gene* 10:157). This plasmid contains the trp1 gene, which provides a selection marker for a mutant strain of yeast lacking the ability to grow in tryptophan, for example ATCC No. 44076 or PEP4-1 (Jones (1977) *Genetics* 85:12). The presence of the trp1 lesion in the yeast host cell genome then provides an effective environment for detecting transformation by growth in the absence of tryptophan.

Suitable promoting sequences in yeast vectors include the promoters for metallothionein, 3-phosphoglycerate kinase (Hitzeman et al. (1980) *J. Biol. Chem.* 255:2073) or other glycolytic enzymes (Hess et al. (1968) *J. Adv. Enzyme Reg.* 7:149; Holland et al. (1978) *Biochemistry* 17:4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are commercially available and further described in Hitzeman et al., EP 73,657.

As will be understood by those of skill in the art, expression vectors containing polynucleotides which encode a degradative enzyme of interest, e.g., a urease or creatininase, can be designed to contain signal sequences which direct secretion of enzyme of interest through a prokaryotic or eukaryotic cell membrane. Such signal sequences are well-established in the art and can be taken from other enzymes/proteins known to be secreted into the extracellular environment.

Transforming the microorganisms as defined herein, describes a process by which exogenous DNA is introduced into and changes a recipient cell. It can occur under natural or artificial conditions using various methods well-known in the art. Transformation can rely on any known method for the insertion of foreign nucleic acid sequences into a prokaryotic or eukaryotic host cell. The method is selected based on the type of host cell being transformed and can include, but is not limited to, viral infection, electroporation, heat shock, lipofection, and particle bombardment. Such "transformed" cells include stably-transformed cells in which the inserted DNA is capable of replication either as an autonomously replicating plasmid or as part of the host chromosome. This also includes cells which transiently express the inserted DNA or RNA for limited periods of time.

As will be appreciated by the skill artisan, a microorganism can also be exposed to a mutagen to cause changes in the genetic structure of the organism so that it expresses elevated levels of a catabolic enzyme of interest.

Transformed or mutagenized strains are subsequently selected for the ability to grow in the presence of the metabolite which is degraded by the catabolic enzyme of interest. By way of example, a strain transformed with nucleic acid sequences encoding a urease is selected for high levels of urease secretion by growing said strain on high levels of urea. Levels of urease secretion can also be detected using standard enzymatic assays. As disclosed herein, the strain can be sequentially subcultured on increasing levels of urea to further enhance urease secretion.

The probiotics according to the invention can be obtained by fermentation and can be stored after fermentation and before addition to the synbiotic composition of the present invention for a time and at a temperature that prevents substantial loss of probiotic cfu. For example, the probiotic component can be fermented until a final concentration of $10^6$ to $10^{10}$ cfu per mL, or $10^7$ to $10^{10}$ cfu per mL, or $10^8$ to $10^9$ cfu per mL of fermented medium is achieved.

When the probiotic component is a mono culture, said mono culture is 100% of the probiotic component. When the probiotic component is composed of at least two or more microorganisms, each microorganism can be 10, 15, 20, 30, 40, 50, 60, 70, 80, or 90% of the probiotic component, wherein the total of all microorganisms is 100%. In certain embodiments, when the probiotic component is composed of two or more microorganisms, each microorganism is present in equal amounts. By way of illustration, a probiotic component can be composed of two microorganisms, wherein each accounts for 50% of the probiotic component. In another illustrative example, a probiotic component can be composed of three microorganisms, wherein each accounts for 33.3% of the probiotic component. In particular embodiments, the probiotic component of the present composition is composed of about 33% *Lactobacillus acidophilus*, 33% *Streptococcus thermophilus*, and 33% *Bifidobacterium longum*. Alternatively stated, the probiotic component of the present composition is composed of *Lactobacillus acidophilus*, *Streptococcus thermophilus*, and *Bifidobacterium longum* at a ratio of 1:1:1.

As used herein, the probiotic component is one component or additive to a food product, tablet, capsule, powder, soft gel, gelcap, or liquid. The probiotic component is included in the composition at a concentration in the range of $10^7$ cfu/mL to $10^{13}$ cfu/mL, $10^8$ cfu/mL to $10^{12}$ cfu/mL, or $10^9$ cfu/mL to $10^{11}$ cfu/mL when added as a liquid or in the range of $10^7$ cfu/g to $10^{13}$ cfu/g, $10^8$ cfu/g to $10^{12}$ cfu/g, or $10^8$ cfu/g to $10^{11}$ cfu/g when added as a freeze-dried powder. More particularly, the probiotic component is included in the composition at a concentration of at least about $10^8$ cfu/mL, $10^9$ cfu/mL, $10^{10}$ cfu/mL, $10^{11}$ cfu/mL, or $10^{12}$ cfu/mL when added as a liquid, or at a concentration of at least about $10^8$ cfu/g, $10^9$ cfu/g, $10^{10}$ cfu/g, $10^{11}$ cfu/g, or $10^{12}$ cfu/g when added as a freeze-dried powder. In certain embodiments, the composition includes at least $1\times10^{10}$ cfu, $1.5\times10^{10}$ cfu, $2\times10^{10}$ cfu, $2.5\times10^{10}$ cfu, $3\times10^{10}$ cfu, $3.5\times10^{10}$ cfu, $4\times10^{10}$ cfu, $4.5\times10^{10}$ cfu, $5\times10^{10}$ cfu, $5.5\times10^{10}$ cfu, $6\times10^{10}$ cfu, $6.5\times10^{10}$ cfu, $7\times10^{10}$ cfu, $7.5\times10^{10}$ cfu, $8\times10^{10}$ cfu, $8.5\times10^{10}$ cfu, $9\times10^{10}$ cfu or $9.5\times10^{1}$ cfu of probiotic bacteria. In some embodiments, the composition is a delayed-lease composition containing $4.5\times10^{10}$ cfu probiotic bacteria.

In a particular embodiment, the composition of the invention is a delayed-lease composition containing $1.5\times10^{10}$ cfu of each of *Lactobacillus acidophilus*, *Streptococcus thermophilus*, and *Bifidobacterium longum*. The selection of *S. thermophilus* for inclusion in the composition is based upon its ability to reduce the levels of urea, uric acid and creatinine in the blood and produce bacteriocins, which inhibit the growth of pathogens. Similarly, *L. acidopilus* is included in the composition given its ability to reduce uric acid, dimethlyamine, trimethlyamine, trimethylamine N-oxide and nitrosoamines in the blood and produce bacteriocin, in particular lactacin. Likewise, *B. longum* is included in the composition to facilitate the reduction of creatinine, indoles and phenols in the blood and produce the bacteriocin bisin. In addition to reducing and metabolizing nitrogenous wastes and uremic toxins, these bacteria reduce the levels of pathogenic bacteria in the imbalanced gut of renal failure patients and modulate the production of various cytokines thereby reducing levels of inflammation (Hardy, et al. (2013) *Nutrients* 5(6):1869-1912). These probiotic bacteria of this invention can be isolated from natural sources, e.g., yogurt or dahi, or obtained from commercial sources such as DuPont (Madison, Wis.), Morinaga & Co. (Tokyo, Japan), and the like.

In the composition of this invention, the probiotic component is about 20% to about 70% of the total composition weight. In particular embodiments, the probiotic component is about 50% of the total composition weight. Likewise, the prebiotic component of the composition is about 20% to about 70% of the total composition weight or more preferably about 50% of the total composition weight.

A prebiotic component of the present invention refers to a non-digestive food that beneficially affects the host by selectively stimulating the growth and/or activity of one or more non-pathogenic bacteria in the colon and/or the growth and/or activity of one or more of the bacteria of the present composition. Prebiotic components of the present invention are considered to have anti-carcinogenic, anti-microbial, hypolipidemic and glucose modulatory activities. They can also improve mineral absorption and balance. Furthermore, bacteria belonging to the *Bifidobacterium* and *Lactobacillus* families are stimulated by the presence of the prebiotic component and proliferate. Pharmacokinetically, prebiotic components reach the colon largely intact. Exemplary prebiotic components include, but are not limited to, inulin and an oligosaccharide such as xylooligosaccharide. Other prebiotic components of use in this invention include fructo-oligosaccharides, isomaltose oligosaccharides, trans-galacto-oligosaccharides, or soy-oligosaccharides; a pyrodextrin such as arabinogalactan, lactitol, lactosucrose, or lactulose; or a fiber source such as oat gum, pea fiber, apple fiber, pectin, guar gum, *psyllium* husks, glucomannan or guar gum hydrolysate (BeneFiber, Novartis Pharmaceuticals).

In particular embodiments, the prebiotic component used in the instant composition is a combination of xylooligosaccharide and inulin. As demonstrated herein, xylooligosaccharide is included as it promotes the growth of *Bifidobacterium* and *Lactobacillus* bacteria. Similarly, inulin is included in the instant composition as it promotes the growth of *bifidobacteria* and also lowers the levels of p-cresol and p-cresyl sulphate in CKD patients (Salmean, et al. (2015) *J. Ren. Nutr.* 25(3):316-320).

When the prebiotic component is a single non-digestive food, said non-digestive food is 100% of the prebiotic component. When the prebiotic component is composed of two or more non-digestive foods, each non-digestive food can be 5, 10, 15, 20, 30, 40, 50, 60, 70, 80, or 90% of the prebiotic component, wherein the non-digestive food total is 100%.

The amount of prebiotic component added to the probiotic component is at least 100 milligrams per serving, 500 milligrams per serving, 1 gram per serving, 5 grams per serving or 10 grams per serving. In one embodiment, the prebiotic component is not less than 100 milligrams and not more than 10 grams per serving. In compositions including xylooligosaccharide and inulin, it is preferred that 60 mg of each of these prebiotics is included in the composition. In another embodiment, the prebiotic component is about 20% to about 70% of the total synbiotic product weight. In particular embodiments, the prebiotic component is about 50% of the total synbiotic product weight. When the synbiotic product further includes addition additives, the percent of the prebiotic and/or probiotic component can be decreased to accommodate the additional additive. In particular embodiments, the percent of the prebiotic component is decreased to accommodate the additional additive.

A synbiotic product or composition combining the beneficial properties of probiotic and prebiotic components can include a food product, dietary supplement, comestible medical food or pharmaceutical product. In the context of the present invention, "synbiotic" refers to a mixture of at least one probiotic and at least one prebiotic components to promote health enhancing effects (Gibson and Roberfroid (1995) *J. Nutr.* 125:1401-1412). The ingestion of said synbiotic product reduces the blood concentration of nitrogenous waste products that accumulate in the circulating blood stream. In particular, it has been observed that a composition composed of *S. thermophilus, L. acidophilus* and *B. longum* (45 billion total) can reduce urea levels by 60% in approximately 24 hours. These waste products can be of an endogenous origin such as normal or abnormal metabolic routes or bacterial putrefaction. Furthermore, the waste products can be of an exogenous origin as in dietary intake of proteins and amino acids. Furthermore, repeated ingestion of the synbiotic product will have a highly beneficial effect upon the intestinal microflora by localization and colonization in the large intestine of microbes known to promote a healthy intestinal microenvironment. In some embodiments of this invention, the synbiotic composition comprises a *Lactobacillus* bacterium, a *Bifidobacterium* bacterium, a *Streptococcus* bacterium, inulin and xylooligosaccharide. In particular embodiments of this invention, the synbiotic composition consists essentially of a *Lactobacillus* bacterium, a *Bifidobacterium* bacterium, a *Streptococcus* bacterium, inulin and xylooligosaccharide, wherein the term "consisting essentially of" or "consists essentially of" means that the activity of the synbiotic is attributed to the *Lactobacillus* bacterium, the *Bifidobacterium* bacterium, the *Streptococcus* bacterium, inulin and xylooligosaccharide and not other, non-essential ingredients such as fillers, additives, excipients, flavors, sweetening agents, binders or bulking agents. In specific embodiments, the synbiotic product consists essentially of *Lactobacillus acidophilus, Bifidobacterium longum,* a *Streptococcus thermophilus*, inulin and xylooligosaccharide.

As indicated herein, a synbiotic product or composition of the present invention can take the form of a food product including, but is not limited to, a health bar, health drink, yogurt, dahi, or sachet or a supplement such as a tablet, capsule, powder, soft gel, gelcap, or liquid. In addition to containing the prebiotic and probiotic components, the synbiotic product of the present invention can further containing various fillers or additives.

Optional additives of the present composition include, without limitation, pharmaceutical excipients such as magnesium stearate, talc, starch, sugars, fats, antioxidants, amino acids, proteins, nucleic acids, electrolytes, vitamins, derivatives thereof or combinations thereof. In some embodiments, the composition includes a vitamin, e.g., vitamin $B_3$ (niacin), zinc, vitamin C, vitamin E, and/or vitamin D. In one embodiment, an additive of the synbiotic product is carob flour, for example, locust bean gum. In another embodiment, an additive is a mushroom extract from *Agaricus bisporus*. In particular embodiments, the composition contains fillers such as magnesium stearate, talc and/or starch. In a still further embodiment, the composition includes a reducing agent such as glutathione or glutamine.

Further, to increase the palatability of a food product containing a prebiotic and probiotic, it may be desirable to add flavors, sweetening agents, binders or bulking agents.

Flavors which can optionally be added to the present compositions are those well-known in the pharmaceutical art. Examples include, but are not limited to, synthetic flavor oils, and/or oils from plants leaves, flowers, fruits and so forth, and combinations thereof are useful. Examples of flavor oils include, but are not limited to, spearmint oil, peppermint oil, cinnamon oil, and oil of wintergreen (methylsalicylate). Also useful are artificial, natural or synthetic fruit flavors such as citrus oils including lemon, orange, grape, lime, and grapefruit, and fruit essences including apple, strawberry, cherry, pineapple and so forth.

Sweetening agents can be selected from a wide range of materials such as water-soluble sweetening agents, water-soluble artificial sweeteners, and dipeptide-based sweeteners, including salts thereof and mixtures thereof, without limitation.

Binders can be selected from a wide range of materials such as hydroxypropylmethylcellulose, ethylcellulose, or other suitable cellulose derivatives, povidone, acrylic and methacrylic acid co-polymers, pharmaceutical glaze, gums (e.g., gum tragacanth), milk derivatives (e.g., whey), starches (e.g., corn starch) or gelatin, and derivatives, as well as other conventional binders well-known to persons skilled in the art. Examples of bulking substances include, but are not limited to, sugar, lactose, gelatin, starch, and silicon dioxide.

When the above-mentioned additives are included in the synbiotic composition of the present invention, they are generally less than 15% of the total synbiotic product weight. In particular embodiments, they are less than 5 to 10% of the total synbiotic product weight.

To facilitate targeting of the composition of this invention to the gastrointestinal tract and protect the bacterium from stomach acids, the composition is provided as a modified-release or delayed-release formulation for oral administration. The term "modified-release" refers to dosage forms whose release characteristics of time course and/or location are chosen to accomplish beneficial or convenience objectives not offered by conventional dosage forms such as a solution or an immediate-release dosage form. Modified-release dosage forms include both delayed- and extended-release drug products. The term "delayed-release" refers to dosage forms that encapsulate or surround an active ingredient and delay release of the active ingredient until the dosage form reaches the small intestine (enteric coated dosage forms) or the colon (colon-specific dosage forms). In this respect, a delayed-release formulation resists release of the active ingredient in gastric fluid, but disintegrates in intestinal fluid.

Modified-release dosage forms include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding modified-release drug delivery systems can be found in Yie W. Chien, Novel Drug Delivery Systems, 1992 (Marcel Dekker, Inc.).

Enteric coatings can be applied to tablets or capsules such that at low pH the coatings remain insoluble. However, as the pH increases in the gastrointestingal tract, the acidic functional groups are capable of ionization, and the polymer swells or becomes soluble in the intestinal fluid. Enteric coatings promote the compounds remaining physically incorporated in the dosage form for a specified period when exposed to gastric juice. Yet the enteric coatings are designed to disintegrate in intestinal fluid. Materials used for enteric coatings include shellac (e.g., esters of aleurtic acid), cellulose acetate phthalate (CAP), poly(methacrylic acid-co-methyl methacrylate, cellulose acetate trimellitate (CAT), poly(vinyl acetate phthalate)(PVAP), hydroxypropyl methylcellulose phthalate (HPMCP), fatty acids, waxes, plastics, plant fibers (e.g., amylose starch) and plant proteins (e.g., zein or AQUA-ZEIN), or dextrins. Various enteric coating materials can be selected on the basis of testing to achieve an enteric-coated dosage form designed ab initio to have a preferable combination of dissolution time, coating thicknesses and diametral crushing strength. (Porter et al. (1970) *J. Pharm. Pharmacol.* 22:42p). It is contemplated that the enteric coating can be either food grade or pharmaceutical material which is generally used in the production of various drug or dietary supplements.

Colon-specific dosage forms protect the active ingredient from release in duodenum and jejunum, and promote eventual release of the active ingredient into ileum or colon. Several approaches are used for site-specific drug delivery including, but not limited to pH-sensitive polymer drug delivery; time-controlled release delivery (see, e.g., Gazzaniga, et al. (1994) *Int. J. Pharm.* 108:77-83; Fukui, et al. (2000) *Int. J. Pharm.* 204(1-2):7-15); microbially triggered drug delivery (see, e.g., Peters, et al. (1993) *Int. J. Pharm.* 94:125-134; Swift (1992) *Proc. ACS Div. Poly. Mat. Sci. Eng.* 66:403-404; Huang, et al. (1979) *J. Appl. Polym. Sci.* 23:429-437); polysaccharide-based drug delivery systems such as chitosan, chitosan derivatives, amidated pectin, and chondroitin sulfate; pressure-controlled drug delivery (see, e.g., Muraoka, et al. (1998) *J. Control. Release* 52(1-2):119-29); novel colon targeted delivery (see, e.g., U.S. Pat. No. 6,368,629; Katsuma, et al. (2004) *J. Pharm. Sci.* 93(5):1287-1299); and osmotic controlled drug delivery (OROS-CT; Alza Corporation).

Depending on whether the synbiotic product is to be consumed by an adult human, child or animal (e.g., companion animal or livestock), it can be produced in various sizes and with various ingredients suitable for the intended recipient. For example, while a gel cap size of 0 or 1 may be suitable for humans, a gel cap size of 2, 3, 4, or 5 may be more suitable for a companion animal.

Further, because the probiotic and prebiotic components of the present invention are generally recognized as safe, they can be consumed one, two or three times daily or more.

The present invention also relates to methods for removing nitrogenous waste products from the blood of a subject of an individual with elevated levels of nitrogen-containing waste products and treating renal failure using the delayed-release composition of the invention. Administration of an effective amount of a delayed-release composition of the present invention has the beneficial effect of decreasing or reducing the levels of nitrogenous waste products in the blood to a normal range. For example, normal levels of creatinine in the blood are in the range of 0.6-1.2 mg/dL, whereas normal blood urea nitrogen (BUN) levels range from 7-18 mg/dL and normal uric acid levels in males and females is in the range of 2.1 to 8.5 mg/dL and 2.0 to 7.0 mg/dL, respectively. According, a subject with elevated creatinine, BUN and/or uric acid levels has levels that are above the normal range. Further, a BUN/creatinine ratio of 5-35 is indicative of normal levels of nitrogenous waste products in the blood. As one of skill in the art can appreciate, means for determining the levels of nitrogenous wastes are well-known to the skilled laboratory clinician.

As products of the present invention can reduce the levels of nitrogenous waste products in the blood of a mammal with chronic renal failure, these compositions are useful in a method for ameliorating renal failure. The method involves administering a product of the present invention to a subject having or at risk of having renal failure. Subjects having or at risk of having renal failure include those with diabetic nephropathy, hypertensive nephrosclerosis, glomerulonephritis, interstitial nephritis, or polycystic kidney disease wherein nephron function is impaired thereby decreasing glomerular filtration rate. Desirably, an effective amount of a product for ameliorating renal failure is an amount sufficient to effect beneficial or desired results, including clinical results, and, as such, an effective amount of a product is one which results in the alleviation or amelioration of one or more symptoms associated with renal failure (e.g., a build up of uremic solutes), diminishment of extent of disease, stabilized (i.e., not worsening) state of disease by supporting healthy bowel function, delay or slowing of disease progression, or amelioration or palliation of the disease state. Amelioration can also mean prolonging survival as compared to expected survival if not receiving treatment. In particular embodiments, the instant composition is administered to a subject with renal failure and a protein deficiency.

It is further contemplated that compositions of the present invention containing proteins and probiotics may have further utility in the providing energy and overall health and well-being in subjects undergoing cancer therapy as well as those with hyperuricemia or gout.

The invention will be further described in the following example, which does not limit the scope of the invention described in the claims.

Example 1: Yogurt Food Product

A yogurt food product can be prepared from one gallon of commercially available whole, homogenized, pasteurized milk which is heated to boiling and quickly allowed to cool to approximately 45° C. To this is added approximately one ounce of yogurt starter culture containing lactic acid bacteria of the genus *Lactobacillus, Streptococcus* and *Bifidobacte-*

*ria*. The mixture is mixed well and allowed to ferment at 37° C. for 10 to 12 hours. Xylooligosaccharide, inulin, whole fruit additives, flavoring, sweetening agents, binders, or other additives can be combined and added to the yogurt to obtain a product of desired consistency or to suit the palette of the prospective consumer. In one embodiment of the present invention, a food product comprises components to meet the special dietary needs of individuals with renal insufficiency.

Example 2: Health Bar

Health bars can be prepared by combining various excipients, such as binders, additives, flavorings, colorants and the like, along with the probiotic (i.e., *Lactobacillus, Streptococcus* and *Bifidobacteria*) and prebiotic component (i.e., xylooligosaccharide and inulin), and mixing to a plastic mass consistency. The mass is then either extruded or molded to form "candy bar" shapes that are then dried or allowed to solidify to form the final product.

Example 3: Medical Food

A medical food can be prepared by combining rolled oats, dehydrated apples, honey, inulin, carob flour, cinnamon, sugar, vanilla extract, and lyophilized cultures of *L. acidophilus, S. thermophilus* and a Bifidobacteria ($10^8$-$10^{10}$ cfu each). These ingredients are mixed in appropriate proportions with xylooligosacchraide and inulin and formed into a rectangular bar approximately 12.5 to 15 centimeters in length, 3 to 4 centimeters in width and 1 centimeter in height and placed into a sterile vacuum oven for 12 to 24 hours to obtain an edible food product of the desired consistency.

Example 4: Dietary Supplement

A dietary supplement of the present invention can be prepared by combining the lactic acid bacteria *Lactobacillus acidophilus* (33%), *Bifidobacteria longum* (33%) and *Streptococcus thermophilus* (33%), aseptically freeze-drying the bacteria and combining the processed bulk bacteria (e.g., about 50% of the total synbiotic product weight) with the prebiotic xylooligosaccharide and inulin component, wherein the final prebiotic component is about 45% of the total synbiotic product weight. Fillers such as magnesium stearate, talc and/or starch (e.g., about 5% of the total synbiotic product weight) are added to the prebiotic and probiotic components and prepared in delayed-release capsules. Approximately 15 to 45 billion CFU of the freeze-dried microorganism is contained in each capsule (i.e., approximately 90 to 135 billion CFU microorganisms per gram) that is coated with an acid resistant polymer by spraying the same over a fluidized bed of capsules. The resulting dietary supplement has a low surface area, is relatively non-porous and can protect the contents therein from low pH as is found in the gastric environment for several hours, and will release the contents into the colon wherein the pH is relatively neutral or slightly alkaline. Advantageously, approximately 90-95% of the microorganisms can survive to be released into the gastric environment.

Example 5: Pharmaceutical Product

A pharmaceutical product can be prepared by aseptically freeze-drying a *Lactobacillus, Streptococcus* and a *Bifidobacterium*, combining the processed bulk microorganisms with the prebiotic component, and preparing the synbiotic product as capsules according to the method of Kim et al ((1988) supra) or tablets, powders, soft gels, gelcaps, or liquids according to standard methods. For example, the prebiotic and probiotic components in each capsule are enterically coated with hydroxy-propylmethyl cellulose phthalate by spraying over a fluidized bed of capsules. The resulting pharmaceutical product has a low surface area, is relatively non-porous and can protect the contents therein from low pH as is found in the gastric environment for several hours, and will release the contents into the bowel wherein the pH is relatively neutral or slightly alkaline.

Example 6: Urease-Secreting Strains of *Streptococcus thermophilus*

This example discloses the isolation and selection of a high level urease-secreting strain of *Streptococcus thermophilus*. Three isolates of gram-positive, lactic acid-producing non-pathogenic cocci of *Streptococcus thermophilus* were isolated from various sources and designated KB4, KB19, and KB25. KB4 was isolated from a probiotic product, KB19 was isolated from a commercial yogurt product and KB25 from Dahi yogurt (from India).

Growth rates and urea hydrolysis of these bacteria in the intestinal pH range (pH 5.5, 6.3 and 7.5) were determined by transferring exponentially growing cultures of KB19, KB4 and KB25 into modified Artificial Intestinal Fluid M2 (AIF, US Pharmacopeia) supplemented with 100 mg/dL filter-sterilized urea, 100 μM $NiCl_2$, 10% MRS broth, dextrose to final concentration of 1%, and 0.3% yeast extract, wherein the initial cell density was $10^9$ cfu/mL. Pancreatin was omitted from the recipe to allow the evaluation of bacterial growth by direct OD600 nm measurement. Urea concentration in the supernatants (% of control) and growth (OD600 nm) were measured every 4 hours.

Concentration of urea in the supernatants of bacterial cultures was measured using the protocol and standards supplied with the Blood Urea Nitrogen Reagent Kit (535, Sigma, St. Louis, Mo.). Urea hydrolysis was monitored by comparing urea-nitrogen concentrations in bacterial supernatants to appropriate control medium incubated in the same conditions and expressed as percent of control. Four to nine independent experiments were conducted and Student t-test was used for statistical analysis.

Under similar assay conditions, exponentially growing cultures of KB19, KB4 and KB25 were inoculated into AIF M2, pH 6.3, supplemented with 100 mg/dL urea and with or without 100 μM $NiCl_2$ at initial cell density of $10^9$ cfu/mL to determine whether the growth and rates of urea hydrolysis by these strains was dependent on the additional $Ni^{++}$. Urea concentration in the supernatants as a % of control and growth (OD600 nm) were measured every 4 hours. Four to nine independent experiments were conducted and Student t-test was used for statistical analysis.

Similarly, it was determined whether the growth and rate of urea hydrolysis of these strains was dependent on urea concentration. Under similar growth conditions exponentially growing cultures of KB19, KB4 and KB25 were inoculated into AIF M2, pH 6.3, supplemented with 100 μM NiCl2 and 100, 200, or 300 mg/dL urea. Urea concentration in the supernatants as a % of the control and growth (OD600 nm) were measured every 4 hours. Four to nine independent experiments were conducted and Student t-test was used for statistical analysis.

The survivability of these KB19, KB4 and KB25 was determined in artificial gastric juice in the presence and absence of urea and dextrose. The average loss in viable cell count after exposure to artificial gastric juice (logs cfu/mL) is shown in Table 2.

TABLE 2

| PH/Additive | KB19 | KB4 | KB25 |
|---|---|---|---|
| 1.4 | 7 | 7 | 7 |
| 2.0 | 7 | 7 | 7 |
| 2.5 | 3 | 4 | 4 |
| 2.5/Urea | 3 | 4 | 4 |
| 2.5/Dextrose | 3 | 3 | 3 |
| 2.5/Urea + Dextrose | 3 | 3 | 3 |
| 3.0 | 2 | 2 | 3 |
| 3.0/Urea | 2 | 3 | 3 |
| 3.0/Dextrose | 1 | 2 | 3 |
| 3.0/Urea + Dextrose | 1 | 2 | 2 |

Initial cell density was $10^7$ cfu/mL. Urea and dextrose concentrations were 10 mg/mL and 1%, respectively.

Further it was determined whether the nutrient composition and availablility had an affect on growth and urea hydrolysis by KB19, KB4, and KB25. Each strain was grown for 24 hours at 37° C. and pH 6.0 in the presence or absence of urea and combinations of nitrogen and carbon sources. This analysis indicated that urea hydrolysis was growth- and pH-dependent and that urea concentrations could be reduced by strain KB19 from 300 mg/dL to 20 mg/dL within 24 hours at pH 6.3 when inoculated in AIF at an initial density of $10^9$ cfu/mL.

Further analysis of S. thermophilus KB19 indicated that this strain could survive a 3 hour exposure to gastric juice, pH 3.0, followed by a 3 hour exposure to 0.3% oxgal, pH 6.0, with only 1 log loss in viability. Remaining viable cells were able to proliferate in AIF M2, pH 6.0, supplemented with 230 mg/dL urea and completely hydrolyzed the urea within less than 18 hours (n=4). All test solutions were supplemented with 230 mg/dL urea and 1% dextrose.

Collectively, these analyses indicated that all three strains studied proliferated in the fed state AIF medium in the pH range from 5.5 to 7.5, characteristic of colon environment; they could all use urea as a sole nitrogen source; and they each catabolized urea in the presence of other nitrogen sources. Urea hydrolysis was growth and pH dependent. Under the conditions tested, the rate of urea hydrolysis was strain-dependent in tests of pH stability: KB19=KB25>KB4; Ni requirement: KB25>KB19>KB4; urea hydrolysis for over 300 mg/dL: KB19=KB25>KB4; and specific nutrients: KB19>KB25>KB4. Further, there was strain-dependent results relating to survivability, wherein in tests of gastric juice stability: KB19>KB4>KB25; and bile stability: KB19>KB4>KB25.

In view of the desirable traits exhibited by the selected S. thermophilus strains, the same methodology can be used to select or train strains of Lactobacillus and Bifidobacterium for increased urease activity. Therefore, in certain embodiments, the Lactobacillus and/or Bifidobacterium of this invention are selected for the ability to reduce urea concentrations from 300 mg/dL to 20 mg/dL within 24 hours at pH 6.3.

Example 7: Growth of Lactobacillus and Bifidobacterium on Oligosaccharides

Pure strains of L. acidophilus and B. longum were grown on growth medium containing the prebiotics xylooligosaccharide and arabinogalactan as the carbon source. The control medium had dextrose as carbon source. After 3 days of incubation at 37° C., bacterial colonies were counted. The results of this analysis indicated that xylooligosaccharide supported the growth of both L. acidophilus and B. longum.

Example 8: Reduction in Uric Acid Levels in Patients with Chronic Kidney Disease (CKD)

A synbiotic product composed of Lactobacillus acidophilus, Streptococcus thermophilus, Bifidobacterium longum and psyllium husks was orally administered to CKD patients in a cross-over experiment, i.e., Group A was provided with the synbiotic product for three months (period 1) and then switched to a placebo for three months (period 2), whereas Group B was provided with a placebo for three months (period 1) and then switched to the synbiotic product for three months (period 2). Biochemical uremic markers (creatinine, uric acid, BUN and CRP) were measured at the end of period 1 and period 2 for each group. The percent of patients showing improvement in uric acid levels upon receiving the synbiotic product is presented in Table 3.

TABLE 3

| Site | No. of Patients | No of Patients with Decreased Levels of Uric Acid (%) | No. of Patients with Improved Quality of Life Ratings (%) |
|---|---|---|---|
| Argentina | 8 | 4 (50) | 7 (88) |
| Canada | 13 | 4 (31) | 11 (85) |
| Nigeria | 15 | 5 (33) | 13 (87) |
| USA | 10 | 2 (20) | 8 (80) |
| Totals | 46 | 15 (33) | 39 (85) |

In a similar crossover study, stage 3 and 4 chronic kidney disease patients were provided dietary supplementation with a synbiotic product composed of Lactobacillus acidophilus, Streptococcus thermophilus, Bifidobacterium longum and psyllium husks. A total of 13 patients completed the study. Blood was drawn from each patient at every monthly visit. Subsequent to the study completion, relative changes in uric acid levels were calculated for both treatment periods and for each patient. Based on this cumulative data from all patients, relative changes based on the administered treatment—symbiotic product or placebo—were pooled and average relative changes for were calculated.

This analysis indicated that there was a significant mean change in uric acid concentration during the synbiotic treatment period (−24.70 μmol/L) versus during the placebo period (50.62 μmol/L, p=0.05). Therefore, a synbiotic product can effectively reduce uric acid levels in the blood.

What is claimed is:
1. A delayed-release composition comprising
    (a) a probiotic component consisting of Lactobacillus acidophilus, Streptococcus thermophilus, and Bifidobacterium longum, wherein the Lactobacillus acidophilus, Streptococcus thermophilus, Bifidobacterium longum are present at a ratio of 1:1:1; and
    (b) a prebiotic component comprising xylooligosaccharide and inulin.
2. The delayed-release composition of claim 1, wherein the Streptococcus thermophilus is selected for the ability to affect at least a 50% reduction in urea concentrations within 24 hours.
3. The delayed-release composition of claim 1, wherein the composition comprises a capsule.

4. The delayed-release composition of claim 1, further comprising a vitamin.

5. The delayed-release composition of claim 1, further comprising a reducing agent.

6. The delayed-release composition of claim 5, wherein the reducing agent is glutathione or glutamine.

\* \* \* \* \*